US012616407B2

(12) United States Patent
Son et al.

(10) Patent No.: US 12,616,407 B2
(45) Date of Patent: May 5, 2026

(54) SHAPE-DEFORMABLE AND ELASTIC BIOADHESIVE ELECTRONIC DEVICE AND MANUFACTURING METHOD THEREOF

(71) Applicant: Research & Business Foundation SUNGKYUNKWAN UNIVERSITY, Suwon-si (KR)

(72) Inventors: Donghee Son, Suwon-si (KR); Mikyung Shin, Suwon-si (KR); Sumin Kim, Suwon-si (KR); Sungjun Lee, Seoul (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 333 days.

(21) Appl. No.: 18/512,565

(22) Filed: Nov. 17, 2023

(65) Prior Publication Data

US 2024/0165293 A1 May 23, 2024

(30) Foreign Application Priority Data

Nov. 17, 2022 (KR) ......................... 10-2022-0154937

(51) Int. Cl.
| | |
|---|---|
| *A61B 5/291* | (2021.01) |
| *A61B 5/257* | (2021.01) |
| (Continued) | |

(52) U.S. Cl.
CPC .............. *A61B 5/291* (2021.01); *A61B 5/257* (2021.01); *A61L 24/0031* (2013.01);
(Continued)

(58) Field of Classification Search
CPC ......... A61B 5/257; A61B 5/263; A61B 5/291; A61B 2562/0209; A61B 2562/135; A61L 24/0031
See application file for complete search history.

(56) References Cited

U.S. PATENT DOCUMENTS

| | | |
|---|---|---|
| 2016/0144608 A1 | 5/2016 | Chang |
| 2018/0192952 A1 | 7/2018 | Rogers et al. |
| 2019/0090801 A1* | 3/2019 | Rogers ................. A61B 5/4836 |

FOREIGN PATENT DOCUMENTS

| | | |
|---|---|---|
| KR | 10-2021-0000643 A | 1/2021 |
| KR | 10-2021-0085230 A | 7/2021 |

(Continued)

OTHER PUBLICATIONS

Korean Office Action issued on Sep. 25, 2024, in counterpart Korean Patent Application No. 10-2022-0154937 (6 pages in English, 6 pages in Korean).

*Primary Examiner* — Eun Hwa Kim
(74) *Attorney, Agent, or Firm* — LEX IP MEISTER, PLLC

(57) ABSTRACT

One embodiment of the present invention provides a shape-deformable and elastic bioadhesive electronic device comprising a self-healing elastomeric polymer substrate, a stretchable thin-film electrode device, and a bioadhesive hydrogel layer. Another embodiment of the present invention provides a method for manufacturing a shape-deformable and elastic bioadhesive electronic device, comprising a transfer printing step of a thin-film electrode device onto a self-healing elastomeric polymer substrate; a substrate separation step of attaching an adhesive tape transferring the thin-film electrode device; an adhesive tape separation step of separating the adhesive tape from the self-healing elastomeric polymer; a pressurization and heat treatment step including heating the separated self-healing elastomeric polymer; and a bioadhesive hydrogel layer forming step of forming a bioadhesive hydrogel layer on a surface of the self-healing elastomeric polymer.

7 Claims, 10 Drawing Sheets

(51) Int. Cl.

| | | |
|---|---|---|
| *A61L 24/00* | (2006.01) | |
| *A61L 24/04* | (2006.01) | |
| *C09J 5/06* | (2006.01) | |
| *A61B 5/263* | (2021.01) | |

(52) U.S. Cl.

CPC ................. *A61L 24/04* (2013.01); *C09J 5/06* (2013.01); *A61B 5/263* (2021.01); *A61B 2562/0209* (2013.01); *A61B 2562/125* (2013.01); *A61L 2400/16* (2013.01); *C09J 2301/12* (2020.08)

(56)                    References Cited

FOREIGN PATENT DOCUMENTS

| KR | 10-2021-0109474 A | 9/2021 |
|----|-------------------|--------|
| KR | 10-2022-0123963 A | 9/2022 |

* cited by examiner

SHAPE-DEFORMABLE AND ELASTIC BIOADHESIVE ELECTRONIC DEVICE AND MANUFACTURING METHOD THEREOF

CROSS REFERENCE TO RELATED APPLICATION

The present application claims priority to Korean Patent Application No. 10-2022-0154937, filed Nov. 17, 2022, the entire contents of which is incorporated herein for all purposes by this reference.

BACKGROUND OF THE INVENTION

Field of the Invention

The present invention relates to a shape-deformable and elastic bioadhesive electronic device and manufacturing method thereof, and more specifically, to a shape-deformable and elastic bioadhesive electronic device capable of conformal osculation to the curved structure of a cerebral cortex and solid adhesion to the tissue surface by incorporating a shape-deformable and elastic bioadhesive patch material, which consists a self-healing elastomeric polymer free to morph its physical shape and a bioadhesive hydrogel capable of tissue-specific adhesion, and a stretchable thin-film electrode device, and a method of manufacturing the same.

Description of the Related Art

Currently, the most advanced patch-type elastic bioelectronic device in the field of brain interfacing sensor technology has been generally manufactured by transfer printing and combining thin-film multi-channel electrode devices encapsulated with polyimide (PI) supports on an elastomeric polymer with surface viscosity and stickiness, such as polydimethylsiloxane (PDMS).

However, due to the insufficient surface stickiness of the PDMS substrate, it was difficult to achieve uniformly adherent transfer printing of the polyimide thin-film device pattern, so there was a challenge that the unity of the substrate and the device could not be maintained and delaminated induced by repeated stretching.

In addition, conventional stretchable elastomeric polymers such as PDMS do not have shape deformability or shape adaptability, so when used as bio-implantable electronic devices, the polymers do not adhere closely to the curvy-linear and complex structures of the cerebral cortex, and it is very difficult for the polymers to be firmly positioned on a wet brain surface, resulting in poor signal measurement and low on-site accuracy of multi-channel sensor devices and unstable biotic-abiotic interfacial impedance property.

In addition, PDMS polymer, which is composed of irreversible covalent bonds, cannot sufficiently dissipate the stress induced by deformation when in contact with the curved cortical surface, thereby inflicting stress to the tissue, causing pressure, foreign body sensation, and discomfort when implanted in the body.

Accordingly, in order to solve the above problems, the inventor has completed the invention of a shape-deformable and elastic bioadhesive electronic device, which is a new type of bioelectronic device that overcomes limitations of the conventional patch-type brain interfacing sensor device incapable of making conformal contact to the curved surface of the cerebral cortex and solid fixation of its position, by integrating micro-patterned stretchable thin-film multi-channel electrode devices onto a functional bilayer patch material that combines self-healing elastomeric polymers and bio-adhesive viscoelastomeric polymers, and a method of manufacturing the same.

SUMMARY

In order to solve the above problems, a technical objective to be achieved by the present invention is to provide a shape-deformable and elastic bioadhesive electronic device comprising a self-healing elastomeric polymer substrate, a stretchable thin-film electrode device, and a bioadhesive hydrogel layer, wherein the self-healing elastomeric polymer substrate is made of a self-healing elastomeric polymer material, in the stretchable thin-film electrode device, one surface and a wall surface connected to the one surface are embedded in the substrate, and a non-embedded wall surface and a portion of the other surface connected to the wall surface are anchored by the material of the substrate, and the bioadhesive hydrogel layer is formed by coating bioadhesive hydrogel on foreside of the embedding-anchoring electrode device.

In order to solve the above problem, another technical objective to be achieved by the present invention is to provide a method for manufacturing a shape-deformable and elastic bioadhesive electronic device, comprising a transfer-printing step of a thin-film electrode device fabricated on a wafer onto a self-healing elastomeric polymer substrate; a substrate separation step of attaching an adhesive tape in a way that transfers the thin-film electrode device delaminated from the wafer to the self-healing elastomeric polymer printed; an adhesive tape separation step of separating the adhesive tape from the self-healing elastomeric polymer substrate on which the thin-film electrode device is printed and to which the adhesive tape is attached; a pressurization and heat treatment step including heating the separated self-healing elastomeric polymer substrate on which the thin-film electrode device is printed and applying pressure to the thin-film electrode device; and a bioadhesive hydrogel layer forming step of forming a bioadhesive hydrogel layer on a surface of the self-healing elastomeric polymer substrate on which the thin-film electrode device that has undergone the pressurization and heat treatment step is printed and the front area where the thin-film electrode device is located.

The technical objectives to be achieved by the present invention are not limited to the technical objectives mentioned above, and other technical objectives not mentioned may be clearly understood by those skilled in the art from the following descriptions.

In order to achieve the above technical objective, an embodiment of the present invention provides a shape-deformable and elastic bioadhesive electronic device comprising a self-healing elastomeric polymer substrate, a stretchable thin-film electrode device, and a bioadhesive hydrogel layer, wherein the self-healing elastomeric polymer substrate is made of a self-healing elastomeric polymer material, in the stretchable thin-film electrode device, one surface and a wall surface connected to the one surface are embedded in the substrate, and a non-embedded wall surface and a portion of the other surface connected to the wall surface are anchored by a material of the substrate, the bioadhesive hydrogel layer is formed by coating bioadhesive hydrogel on the embedded-anchored electrode device.

In an embodiment of the present invention, the self-healing elastomeric polymer material may be a thermoplastic material.

In an embodiment of the present invention, the self-healing elastomeric polymer material may be a material that is elastic and capable of self-healing.

In an embodiment of the present invention, the other surface of the stretchable thin-film electrode device, which is not embedded, may have a pattern consisting of embossing and intaglio, and a portion of the embossing pattern present on the other surface connected to the wall surface may be anchored by a substrate material.

In an embodiment of the present invention, the bioadhesive hydrogel layer may be one or more materials selected from the material groups that are able to be manufactured in a film form and are able to be hydrogelated in a moisture environment, among natural polymers containing aromatic substances and phenols.

In an embodiment of the present invention, a biological tissue to which the shape-deformable and elastic bioadhesive electronic device is applicable may be one or more selected from the group consisting of brain tissue, spinal cord tissue, heart tissue, peripheral nerve tissue, vagus nerve tissue, and muscle tissue.

In an embodiment of the present invention, the thin-film electrode device may be a thin-film multi-channel electrode device.

In order to achieve the above technical objective, another embodiment of the present invention provides a method for manufacturing a shape-deformable and elastic bioadhesive electronic device, comprising a transfer printing step of a thin-film electrode device fabricated on a wafer onto a self-healing elastomeric polymer substrate; a substrate separation step of attaching an adhesive tape transferring the thin-film electrode device delaminated from the wafer to the self-healing elastomeric polymer printed; an adhesive tape separation step of separating the adhesive tape from the self-healing elastomeric polymer substrate on which the thin-film electrode device is printed and to which the adhesive tape is attached; a pressurization and heat treatment step including heating the separated self-healing elastomeric polymer substrate on which the thin-film electrode device is printed and applying pressure to the thin-film electrode device; and a bioadhesive hydrogel layer forming step of forming a bioadhesive hydrogel layer on a surface of the self-healing elastomeric polymer substrate on which the thin-film electrode device that has undergone the pressurization and heat treatment step is printed and the front area where the thin-film electrode device is located.

In an embodiment of the present invention, the method may further comprise, between the pressurization step and the hydrogel layer forming step, a sterilization step of sterilizing the surface of the self-healing elastomeric polymer substrate on which the thin-film electrode device is printed, where the thin-film electrode device is located; and a plasma treatment step of plasma treating the surface of the self-healing elastomeric polymer substrate on which the sterilized thin-film electrode device is printed, where the thin-film electrode device is located.

In an embodiment of the present invention, a temperature of the heating in the pressurization step may be 40 to 80° C.

In an embodiment of the present invention, the pressure in the pressurization step may be a pressure such that in the thin-film electrode device, one surface and a wall surface connected to the one surface are embedded in the substrate, and a non-embedded wall surface and a portion of the other surface connected to the wall surface are anchored by a substrate material.

In an embodiment of the present invention, the plasma in the plasma treatment step may be oxygen plasma.

DETAILED DESCRIPTION

Figure 1:
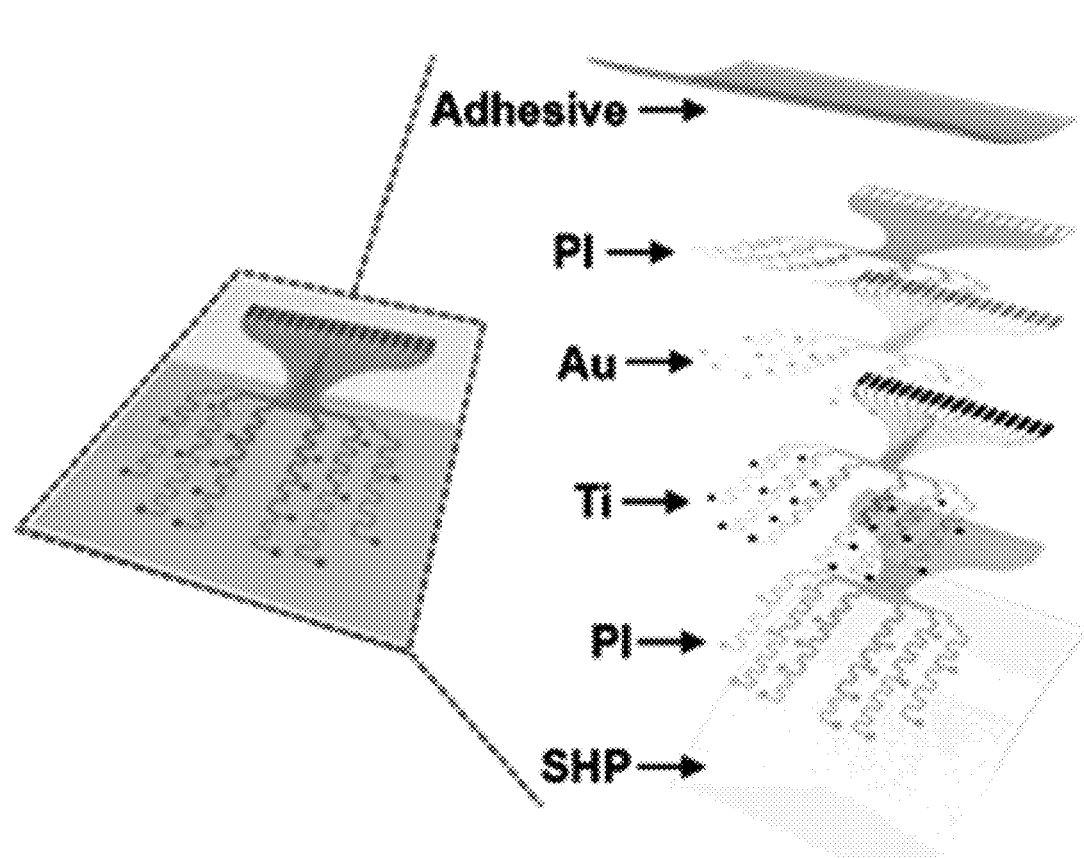
FIG. 1 is a diagram showing the configuration of a shape-deformable and elastic bioadhesive electronic device according to an embodiment of the present invention.

Hereinafter, the present invention will be explained with reference to the accompanying drawings. The present invention, however, may be modified in various different ways, and should not be construed as limited to the embodiments set forth herein. Also, in order to clearly explain the present invention, portions that are not related to the present invention are omitted, and like reference numerals are used to refer to like elements throughout.

Throughout the specification, it will be understood that when an element is referred to as being "connected (accessed, contacted, coupled) to" another element, it may be not only "directly connected to" the other element, but also "indirectly connected to" the other element with intervening elements in between. Also, it will also be understood that when a component "includes" an element, unless stated otherwise, it should be understood that the element does not exclude other elements. In addition, "part by molar weight" refers to the relative number of moles of another constituent measurement subject relative to the number of moles of one reference measurement subject. In this case, the reference measurement subject may be one of the configuration measurement subjects.

Terms used in the present specification are used only to describe specific exemplary embodiments, not being intended to limit the present invention. A singular form may include a plural form if there is no clearly opposite meaning in the context. In this specification, it should be understood that the term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Hereinafter, an embodiment of the present invention will be described in more detail with reference to the accompanying drawings.

In order to solve the above technical problems, one embodiment of the present invention provides a shape-deformable and elastic bioadhesive electronic device comprising a self-healing elastomeric polymer substrate, a stretchable thin-film electrode device, and a bioadhesive hydrogel layer, wherein the self-healing elastomeric polymer substrate is made of a self-healing elastomeric polymer material, in the stretchable thin-film electrode device, one surface and a wall surface connected to the one surface are embedded in the substrate, and a non-embedded wall surface and a portion of the other surface connected to the wall surface are anchored by the material of the substrate, the bioadhesive hydrogel layer is formed by coating bioadhesive hydrogel on the embedded-anchored electrode device.

The embedding may mean that the thin-film electrode device is buried in the substrate, and the anchoring may mean that the material of the substrate surrounds a wall of the thin-film electrode device and a portion of the other surface connected to the wall. In the stretchable thin-film electrode device, one surface and a wall surface connected to the one surface are embedded in the substrate, and the non-embedded wall surface and a portion of the other surface connected to the wall surface are anchored by the substrate material, so that a very uniform, conformal, and robust assembly may be formed across the entire surface of the device. By forming the bioadhesive hydrogel layer, it can adhere perfectly without gaps along the curved tissue surface and form a strong bond to the surface.

In an embodiment of the present invention, the self-healing elastomeric polymer material may be a thermoplastic material. The self-healing elastomeric polymer material is a thermoplastic material, so during the manufacturing process, one surface and wall surface connected to the one surface of the thin-film electrode device are embedded in the substrate, and the non-embedded wall surface and a portion of the other surface connected to the wall surface may be anchored by the substrate material.

The self-healing elastomeric polymer material is a modified silicone polymer material such as PDMS, which has elasticity, as a backbone, and is composed of a multi-structure of reversible chemical bonds such as hydrogen bonds. The self-healing elastomeric polymer material may be a material capable of self-healing by spontaneously dynamically reorganizing chemical bonds at the point of damage in case of the occurrence of physical damage such as cracking or fracture.

In an embodiment of the present invention, the other surface of the stretchable thin-film electrode device, which is not embedded, has a pattern consisting of embossing and intaglio, and a portion of the embossing of the pattern present on the other surface connected to the wall surface may be anchored by the substrate material. A portion of the embossing of the pattern present on the other surface connected to the wall is anchored by the substrate material, allowing complete adhesion of the entire area of the electrode device along the curved tissue surface without any gaps and forming a firm bond on the surface.

In an embodiment of the present invention, the bioadhesive hydrogel layer may be one or more materials selected from the material groups that can be manufactured in a film form and can be hydrogelated in a moisture environment, among natural polymers containing aromatic substances and phenols.

In an embodiment of the present invention, a biological tissue to which the shape-deformable and elastic bioadhesive electronic device is applicable may be one or more selected from the group consisting of brain tissue, spinal cord tissue, heart tissue, peripheral nerve tissue, vagus nerve tissue, and muscle tissue.

In an embodiment of the present invention, the thin-film electrode device may be a thin-film multi-channel electrode device.

In order to achieve the above technical problem, another embodiment of the present invention provides a method for manufacturing a shape-deformable and elastic bioadhesive electronic device, comprising a transfer printing step of a thin-film electrode device fabricated on a wafer onto a self-healing elastomeric polymer substrate; a substrate separation step of attaching an adhesive tape transferring the thin-film electrode device delaminated from the wafer to the self-healing elastomeric polymer printed; an adhesive tape separation step of separating the adhesive tape from the self-healing elastomeric polymer substrate on which the thin-film electrode device is printed and to which the adhesive tape is attached; a pressurization and heat treatment step including heating the separated self-healing elastomeric polymer substrate on which the thin-film electrode device is printed and applying pressure to the thin-film electrode device; and a bioadhesive hydrogel layer forming step of forming a bioadhesive hydrogel layer on a surface of the self-healing elastomeric polymer substrate on which the thin-film electrode device that has undergone the pressurization and heat treatment step is printed and the front area where the thin-film electrode device is located.

Through the pressurization step, a very uniform, conformal, and robust assembly may be formed across the entire surface of the device. By forming the bioadhesive hydrogel layer, it can adhere perfectly without gaps along the curved tissue surface and form a strong bond to the surface.

In an embodiment of the present invention, the method may further comprise, between the pressurization step and the hydrogel layer forming step, a sterilization step of sterilizing the surface of the self-healing elastomeric polymer substrate on which the thin-film electrode device is printed, where the thin-film electrode device is located; and a plasma treatment step of plasma treating the surface of the self-healing elastomeric polymer substrate on which the sterilized thin-film electrode device is printed, where the thin-film electrode device is located.

In an embodiment of the present invention, the heating temperature in the pressurization step may be 40 to 80° C.

In an embodiment of the present invention, the pressure in the pressurization step may be a pressure such that in the thin-film electrode device, one surface and a wall surface connected to the one surface are embedded in the substrate, and a non-embedded wall surface and a portion of the other surface connected to the wall surface are anchored by the substrate material.

In an embodiment of the present invention, the plasma in the plasma treatment step may be oxygen plasma.

Hereinafter, the above-described embodiments will be described in more detail through Examples or Experimental Examples. However, the following Examples or Experimental Examples are for illustrative purposes only and do not limit the scope of the present invention.

EXAMPLES

1. Transfer Printing of Thin-Film Multi-Channel Electrode Devices onto Self-Healing Elastomeric Polymer Substrate Material A thin-film multi-channel electrode device fabricated through a micro-patterning process on wafers are transfer-printed on a self-healing elastomeric polymer substrate material. The device is separated from the wafer using an adhesive tape that dissolves in water or is separated by heat. After attaching the tape that picked up the devices onto the self-healing elastomeric polymer substrate, the tape was separated and removed by dissolving the tape in water or heating it depending on the type of tape used, so that the electrode device is transfer-printed onto the surface of a self-healing elastomeric polymer substrate. The electrode patch device transfer-printed on the self-healing elastomeric polymer substrate is gently pressed by a Teflon-treated plate for 10 to 15 minutes with a thermal treatment of temperature ranging 50 to 70° C., resulting in the shape deformation of the thermoplastic self-healing elastomeric polymer substrate due to heat energy and pressure energy. The transfer-printed electrode device pattern physically penetrates the surface of the self-healing elastomeric polymer substrate material, whose surface properties have become softer due to thermal energy, and the self-healing elastomeric polymer substrate material undergoes shape deformation due to compression and travels along the wall surface of the electrode device, thereby anchoring the boundary between the substrate material and the device pattern. Accordingly, the electronic device is embedded in the substrate surface, forming a very uniform, conformal, and robust assembly across the entire device pattern.

FIG. 1 is a diagram showing the configuration of a shape-deformable and elastic bioadhesive electronic device according to an embodiment of the present invention.

Referring to FIG. 1, an image of the combined state of the shape-deformable and elastic bioadhesive electronic device and each separated thin-film layer can be identified.

Meanwhile, in thermosetting polymer materials such as conventional PDMS, it is impossible to implement coupling by anchoring and surface embedding at the device-substrate boundary due to their lack of shape deformation property. When transferring a thin-film device onto PDMS, the electronic device is attached and fixed to substrate via surface stickiness, so the assembly between the substrate and the device is not uniform, and since the surface stickiness of the PDMS substrate is not sufficient to stably fix the printed device for a long period of time, it is difficult to ensure operational stability when repeated stretching and deformation occur due to its poor coupling durability.

Figure 2:
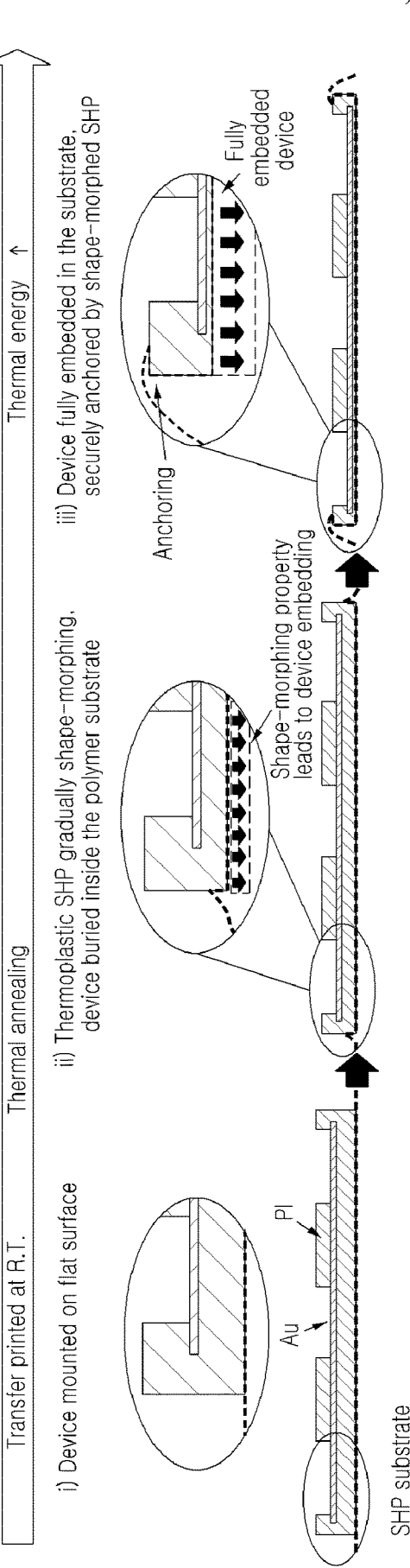
FIG. 2 is a diagram showing the anchoring and embedding process of a thin-film electrode device transfer-printed on a self-healing elastomeric polymer substrate according to an embodiment of the present invention.

FIG. 2 is a diagram showing the anchoring and embedding process of a thin-film electrode device transfer-printed on a self-healing elastomeric polymer substrate according to an embodiment of the present invention.

Referring to FIG. 2, the schematic diagram below shows a process of transfer-printing of a thin-film multi-channel gold electrode device pattern encapsulated with a PI support onto a self-healing elastomeric substrate, and then anchoring and surface embedding of the electrode device onto the self-healing elastic polymer substrate by inducing shape deformation through thermal treatment.

Figure 3:
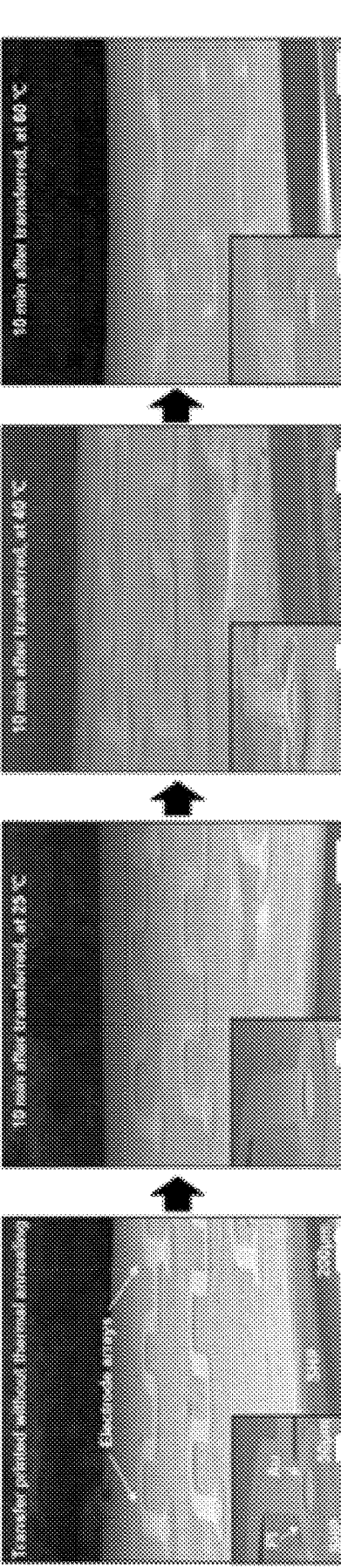
FIG. 3 is a diagram showing the anchoring and embedding of a thin-film electrode device onto a self-healing elastomeric polymer substrate by heat treatment according to an embodiment of the present invention.

FIG. 3 is a diagram showing the anchoring and embedding of a thin-film electrode device onto a self-healing elastomeric polymer substrate by thermal treatment according to an embodiment of the present invention.

Referring to FIG. 3, the obtained scanning electron microscopy images of the shape structure according to thermal treatment of different temperature conditions show the progress of anchoring formation at the substrate-device boundary and embedding of the device pattern into the substrate surface due to the shape deformation of the substrate in the thin-film multi-channel electrode device pattern transfer-printed on the self-healing elastomeric polymer substrate material. When the thermal treatment time is the same at 10 minutes, as the heat energy applied increases in the order of room temperature (25° C.), 40° C., and 60° C. immediately after transfer printing, the anchoring of the wall surface of the electrode device and the embedding into the surface of the self-healing elastomeric polymer substrate proceed proportionally.

2. Formation of a Bioadhesive Hydrogel Layer

Once the assembly of the self-healing elastomeric polymer substrate and the multi-channel thin-film electrode device is completed, a dispersion solution of alginate-catechol hydrogel polymer, a naturally-derived biological tissue adhesive material, uniformly dissolved at a concentration of 2.5% in a water solvent is coated over the multi-channel electrode channel area. Before hydrogel coating, the surface of the thin-film device patch is sterilized through UV treatment for 1 hour. In order to increase the surface affinity when coating the adhesive hydrogel aqueous solution, the surface of the electrode device patch is made hydrophilic through oxygen plasma treatment. After covering a mold with an area of 12*8 mm² where the multi-channel electrode device channels are deployed, 150 µL of hydrogel aqueous solution is poured into the inner area of the mold and is coated evenly over the entire surface. The electrode device patch coated with the hydrogel aqueous solution is solvent-dried on a clean bench for more than half a day, so that a shape-deformable and elastic bioadhesive electronic device (hereinafter referred to as "a shape-deformable electronic sticker patch device" or "a shape-deformable and elastic electronic sticker") is completed.

Figure 4:
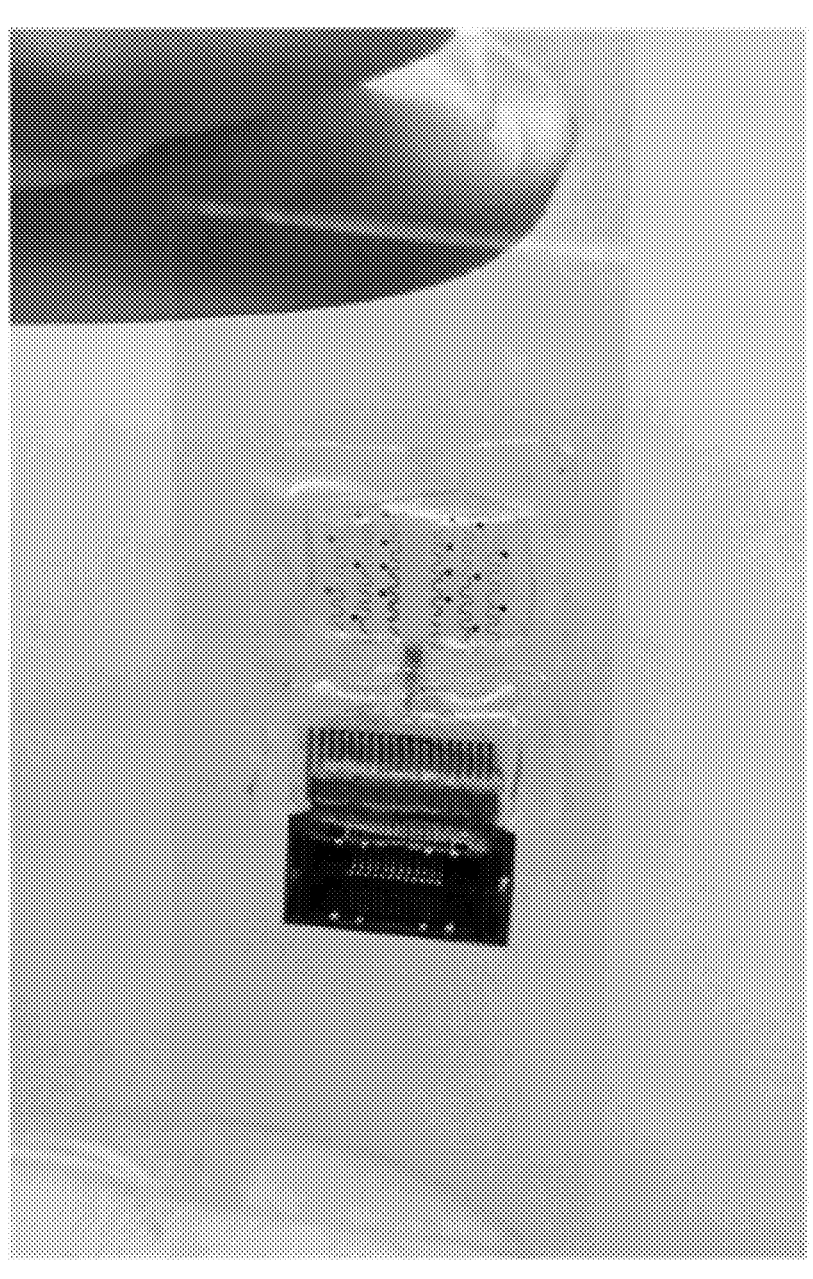
FIG. 4 is a diagram showing a photograph of a shape-deformable and elastic bioadhesive electronic device according to an embodiment of the present invention.

FIG. 4 is a diagram showing a photograph of a shape-deformable and elastic bioadhesive electronic device according to an embodiment of the present invention.

Referring to FIG. 4, a photograph of an implantable cortical-interfacing electrode device which is implemented by connecting a manufactured shape-deformable and elastic bioadhesive electronic device and a multi-channel connector can be identified.

Experimental Example

1. Verification of the elasticity and cortical adhesion of shape-deformable and elastic bioadhesive electronic devices, and the formation of a bio-electronic adhesion interface according to shape deformation, and examples of utilization of a cortex interfacing.

Figure 5:
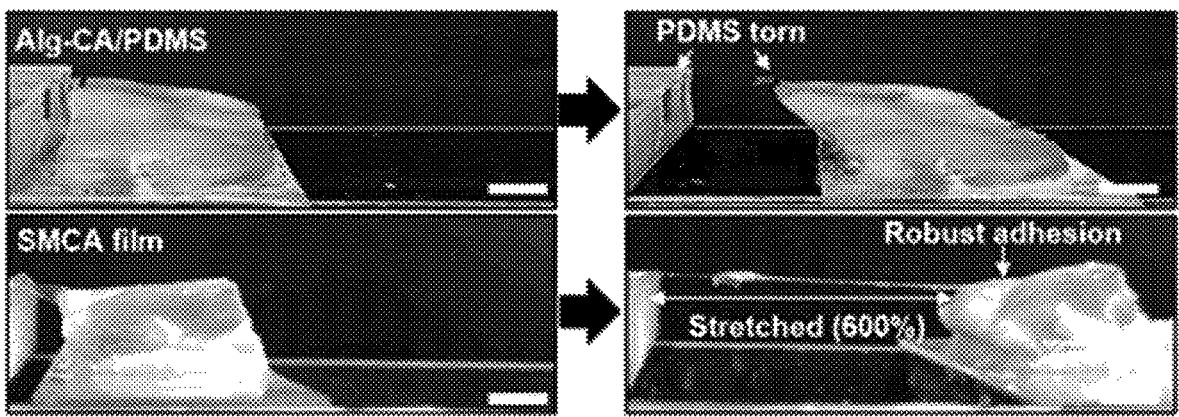
FIG. 5 is a diagram showing the high elasticity and strong adhesive properties of a shape-deformable and elastic bioadhesive patch material according to an embodiment of the present invention.

FIG. 5 is a diagram showing the high elasticity and strong adhesive properties of a shape-deformable and elastic bio-adhesive patch material according to an embodiment of the present invention.

Referring to FIG. 5, the manufactured shape-deformable and elastic bioadhesive electronic device shows excellent adhesion and elasticity when applied to cortical tissue. In the photo below, the top image shows the ability to maintain elasticity and adhesion of the electronic device until a tensile strain of 600% occurs when the electronic device is attached to the cortical surface. The conventional PDMS polymer does not have the viscoelastic and dynamic stress relaxation properties such as those of the self-healing elastomeric polymer, so PDMS does not sufficiently dissipate the stress energy generated during tensile deformation, so it does not maintain elasticity for a long time and is broken.

Figure 6:
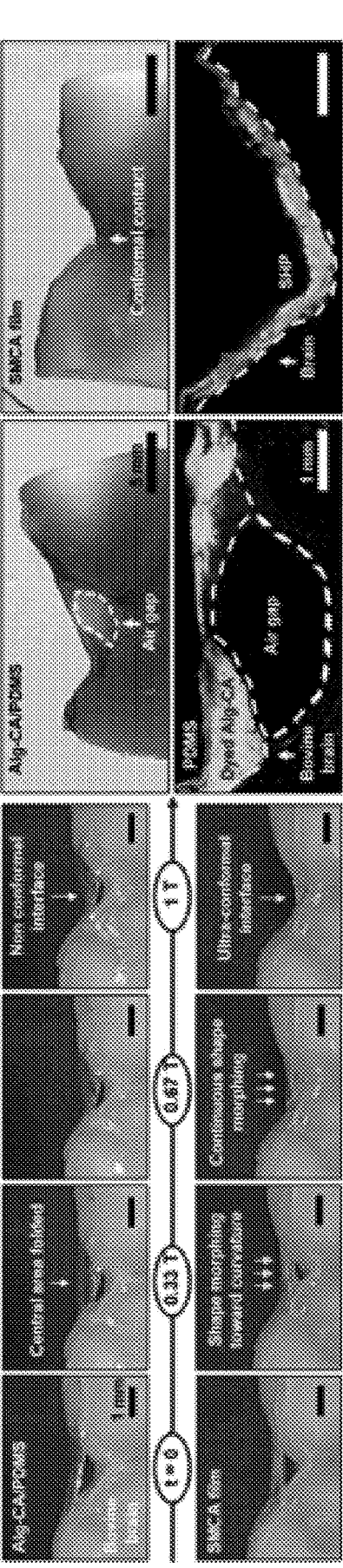
FIG. 6 is a diagram showing the formation of a tight adhesion interface to the curved surface of a cerebral cortex due to shape deformation according to an embodiment of the present invention.

FIG. 6 is a diagram showing the formation of a tight adhesion interface on the curved cortical surface due to shape deformation according to an embodiment of the present invention.

Referring to FIG. 6, the shape-deformable and elastic bioadhesive electronic device may form tight adhesion and complete integration along the morphology of a curved structure with significant steps. The bottom left image shows that when the electronic device is attached to the surface of the bovine brain, it undergoes shape deformation over time without the application of additional physical pressure, entering a deep groove and tightly covering surface profile to form conformal osculation and bio-electronic integration. It can be seen that the conventional PDMS thermosetting polymer does not have the shape deformation property, making it impossible to adhere to the curved structure even over time (top left image). The image on the right is a fluorescence image showing the formation of a conformal adhesion interface of a shape-deformable bioadhesive material with excellent step coverage property (right image). In the case of PDMS, it can be seen that conformal contact is not possible for similar curved surface structures because the shape does not deform (left image).

Figure 7:
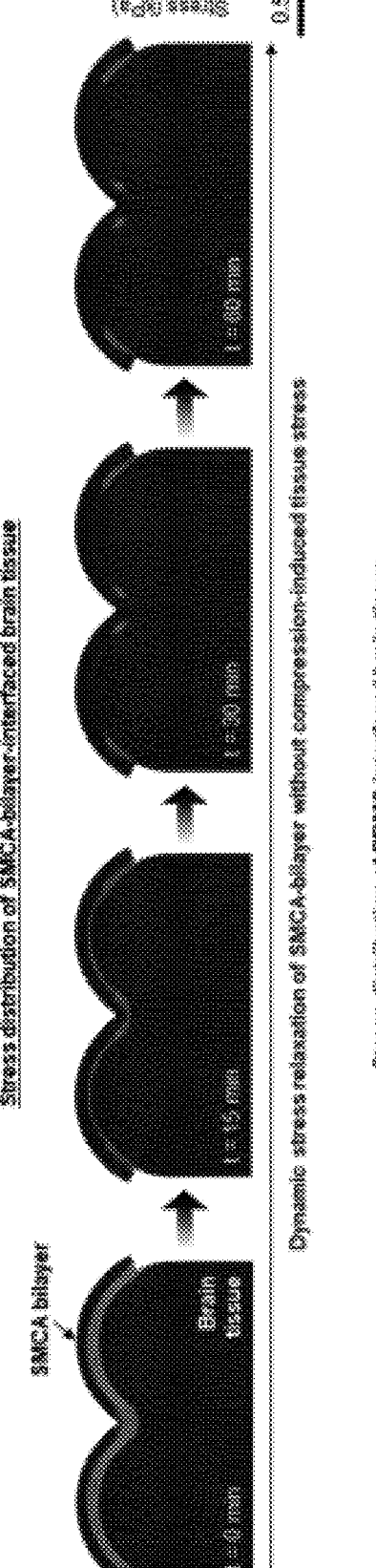
FIG. 7 is a diagram showing the result of a finite element analysis (FEA) simulation showing the self-adaptation characteristics of a shape-deformable and elastic bioadhesive patch material according to an embodiment of the present invention and PDMS with respect to the curved biological tissue surface shape.
Figure 7:
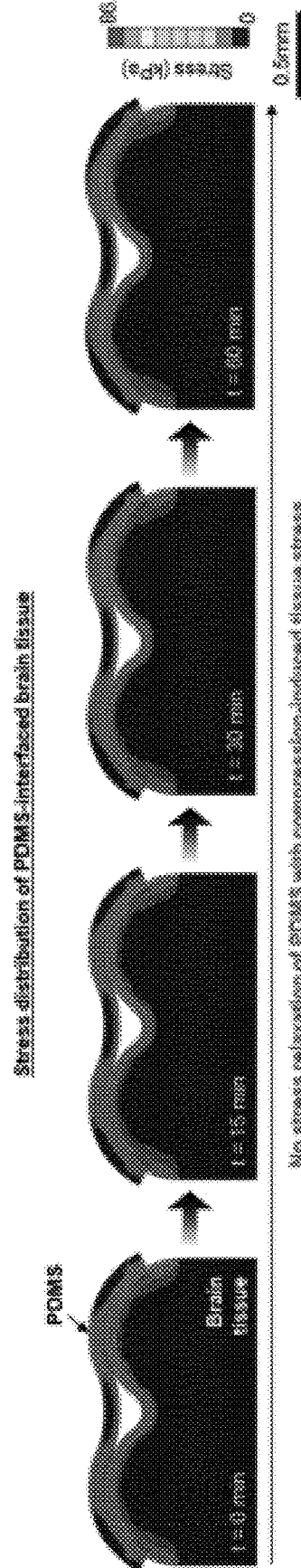

FIG. 7 is a diagram showing the result of a finite element analysis (FEA) simulation showing the self-adaptation behavior of a shape-deformable and elastic bioadhesive patch material according to an embodiment of the present invention and that of PDMS with respect to the curved biological tissue surface shape.

Referring to FIG. 7, the shape-deformable and elastic bioadhesive patch material has self-adaptive property that efficiently dissipate tensile strain energy generated while deforming along the curved cortical surface due to dynamic stress relaxation property and does not apply stress to the tissue in contact. The image below is a finite element analysis (FEA) simulation result showing the self-adaptive property of the shape-deformable and elastic bioadhesive patch material that dissipates most of the tensile strain stress generated as it adheres to the curved surface of the biological tissue over time while not applying stress to the tissue in contact (top). In the case of PDMS, it has no dynamic relaxation property, showing that stress is continuously inflicted to the tissue (bottom).

Figure 8:
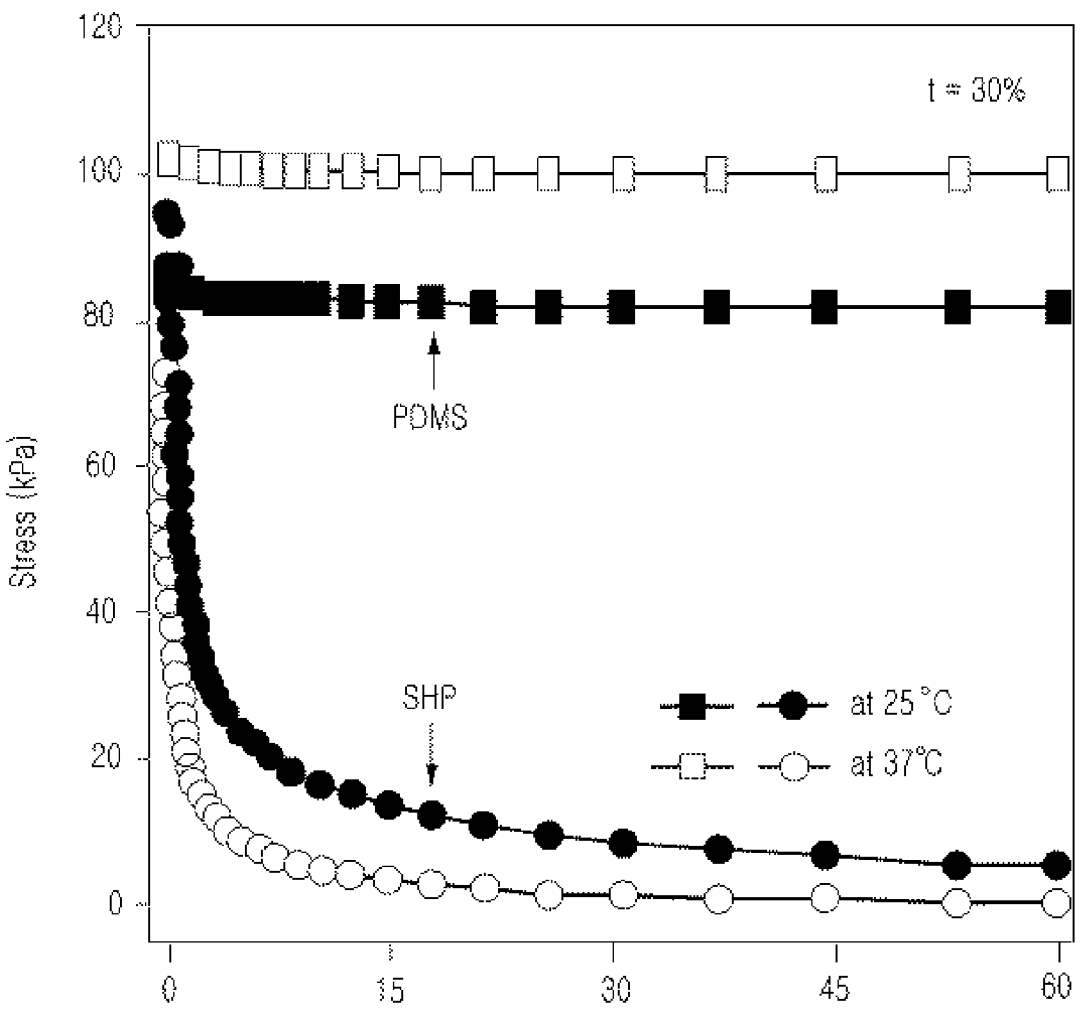
FIG. 8 is a diagram showing stress dissipation due to the dynamic stress relaxation characteristics of a self-healing elastomeric polymer substrate according to an embodiment of the present invention.

FIG. 8 is a diagram showing stress dissipation due to the dynamic stress relaxation property of a self-healing elasto-meric polymer substrate according to an embodiment of the present invention.

Referring to FIG. 8, as an experimental result of FEA simulation analysis, it can be confirmed that the self-healing elastomeric polymer has self-stress relaxation property that efficiently dissipate the stress energy applied to the material during tensile deformation over time. The graph shows the behavior of relieving most of the tensile strain stress applied over 60 minutes when an elastomeric polymer substrate is stretched by 30%. In the case of PDMS, the energy generated during deformation cannot be dissipated, so the stress remains.

Figure 9:
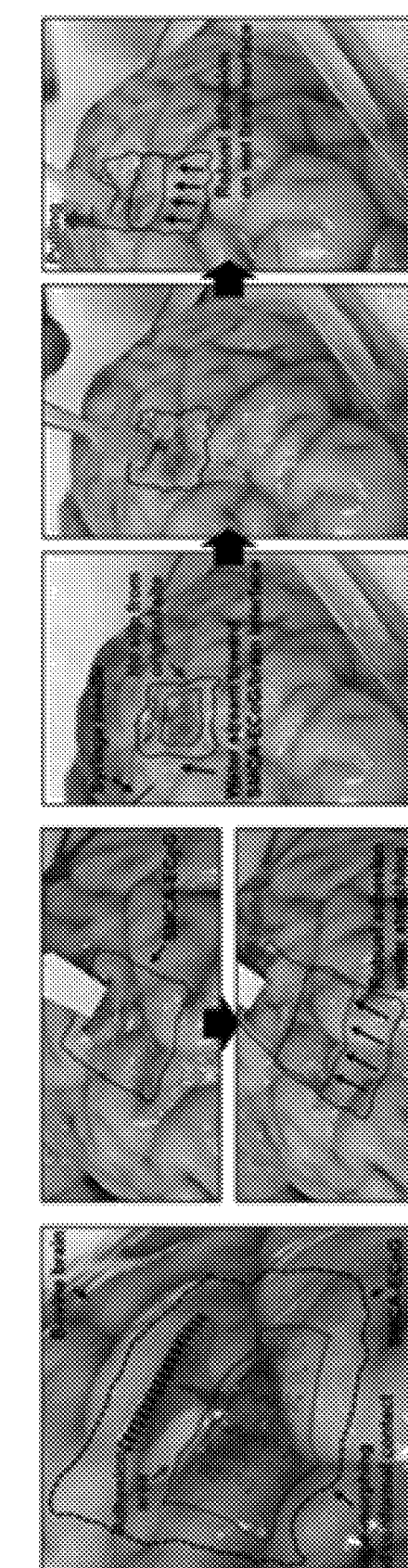
FIG. 9 is a diagram showing shape deformation, formation of a conformal contact interface, and robust adhesion characteristics along the curved surface of a cerebral cortex according to an embodiment of the present invention.

FIG. 9 is a diagram showing shape deformation, formation of a conformal osculation, and robust adhesion property along the curved cortical surface according to an embodiment of the present invention.

Referring to FIG. 9, a shape-deformable and elastic bioadhesive electronic device was implemented by combining the shape-deformable and elastic bioadhesive patch material verified through the above-described process and a multi-channel thin-film electrode device. When the electronic device is applied ex vivo to bovine brain, tissue adhesion can be confirmed to be firmly maintained even with immediate shape deformation and conformal interface formation, tensile strain composition, and in the environment washed down with PBS. In the photo below, the image on the left shows the formation of a fully coupled bio-electronic interface as the electronic device deforms along the curved cortical surface upon contact with bovine brain, completely adapting to the surface shape and achieving tight adhesion. The image in the center shows that the electronic device is firmly attached by gelation of the adhesive hydro-gel immediately after contact with the tissue surface, thereby maintaining the original attachment position even upon application of tensile strain. The image on the right shows the adhesion property to the cerebral cortex that is robustly maintained even after the attached electronic device is washed down by syringe-sprayed PBS.

Figure 10:
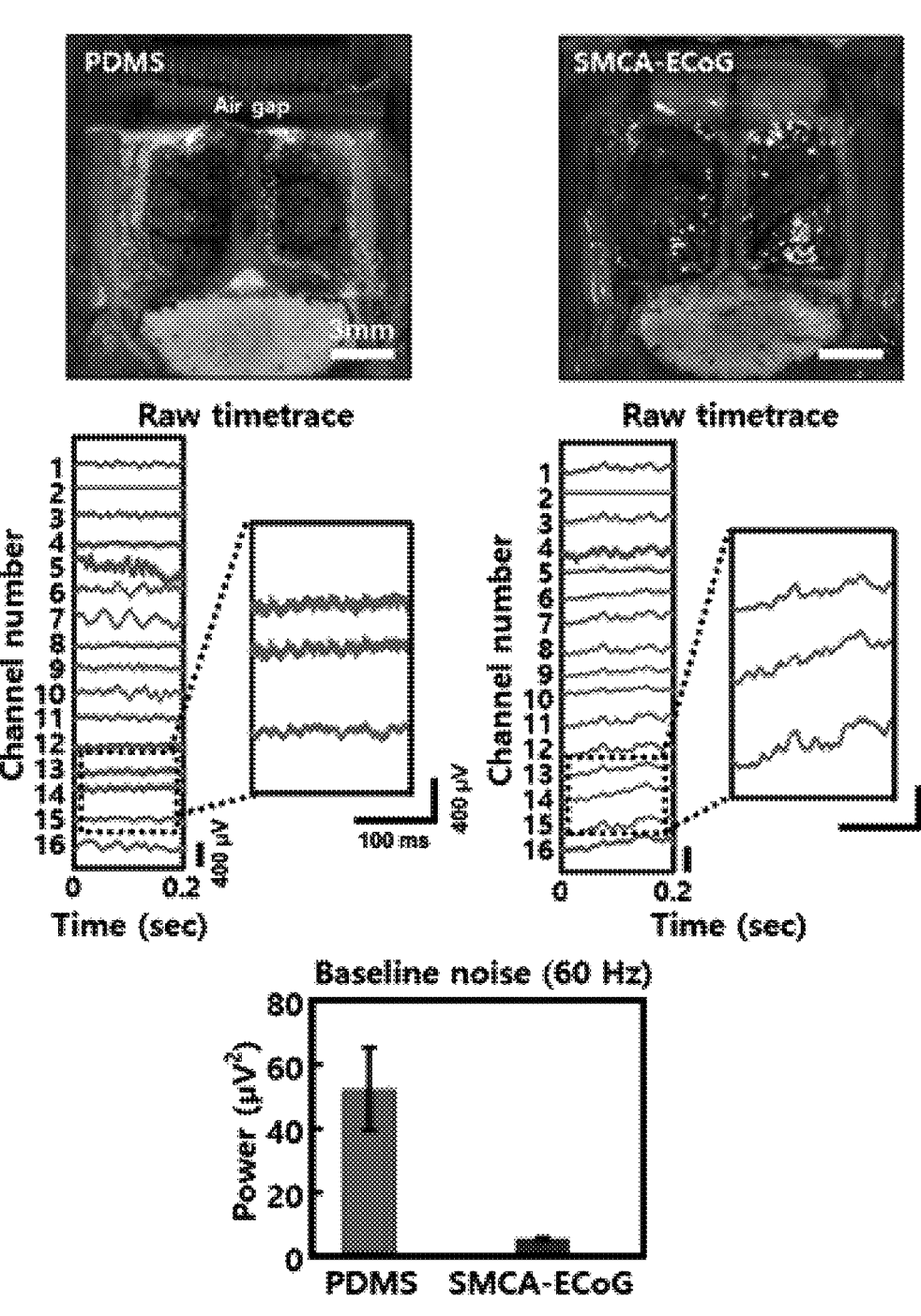
FIG. 10 is a diagram showing the excellent cerebral cortex-integration property and high acquisition performance of brain signal due to the formation of intimate neuro-electronic interface of a shape-deformable and elastic bioadhesive electronic device according to an embodiment of the present invention.

FIG. 10 is a diagram showing the excellent cerebral cortex-integration property and high acquisition performance of brain signal due to the formation of intimate neuro-electronic interface of a shape-deformable and elastic bioadhesive electronic device according to an embodiment of the present invention.

Referring to FIG. 10, the shape-deformable and elastic bioadhesive electronic device has excellent elasticity, cortex adhesion performance, and conformal osculation property, resulting in high acquisition performance of brain signals (right photo and graph). In the case of the patch device using PDMS as a substrate, it does not have conformal adhesion characteristics due to shape deformation like the self-healing elastomeric polymer substrate, so when the patch device is applied to the cerebral cortex, the contact interface is very poor due to the occurrence of a severe air gap, and the acquisition performance of brain signals is poor due to these impedance interface characteristics (left photo and graph). The image below is a graph quantifying the average power of baseline noise using baseline brain signal measurement data conducted over 100 times. Compared to PDMS, the shape-deformable and elastic bioadhesive electronic device shows a very low and stable baseline noise level, demonstrating excellent brain signaling performance.

According to an embodiment of the present invention, the shape-deformable and elastic bioadhesive electronic device is attached by immediate gelation of the bioadhesive hydro-gel upon contact with the cerebral cortex and may have robust positioning due to its high bio-specific adhesive strength characteristics.

In this case, the high biocompatibility of the adhesive hydrogel and the low mechanical properties at the level of the cerebral cortex form a biocompatible neuro-electronic interface and do not induce immune or inflammatory reactions.

In addition, due to its high elasticity and thermoplasticity, the electronic device forms a stable interface by tightly adhering to the highly curved surface of the cerebral cortex, which has a twisted and complex structure with a continuous arrangement of ridges and furrows, so that a multi-channel electrode device may exhibit high acquisition performance of brain signals.

In addition, the high dynamic stress relaxation characteristics of the self-healing elastomeric polymer substrate material effectively dissipate the stress that occurs when the electronic device is deformed along the curved shape of the cerebral cortex, thereby preventing the application of compressive stress to the cerebral cortex in contact. Thus, the electronic device has self-adaptation property that do not cause tissue damage or side effects even when implanted in the body for a long period of time.

The effects of the present disclosure are not limited to the above-mentioned effects, and it should be understood that the effects of the present disclosure include all effects that could be inferred from the configuration of the invention described in the detailed description of the invention or the appended claims.

The description of the present invention is used for illustration and those skilled in the art will understand that the present invention can be easily modified to other detailed forms without changing the technical spirit or an essential feature thereof. Therefore, the aforementioned exemplary embodiments are all illustrative in all aspects and are not limited. For example, each component described as a single type may be implemented to be distributed and similarly, components described to be distributed may also be implemented in a combined form.

The scope of the invention is to be defined by the scope of claims provided below, and all variations or modifications that can be derived from the meaning and scope of the claims as well as their equivalents are to be interpreted as being encompassed within the scope of the present invention.

What is claimed is:

1. A shape-deformable and elastic bioadhesive electronic device comprising:

a self-healing elastomeric polymer substrate;

a stretchable thin-film electrode device; and a bioadhesive hydrogel layer, wherein the self-healing elastomeric polymer substrate is made of a self-healing elastomeric polymer material, wherein the stretchable thin-film electrode device defines an upper surface, a lower surface and a wall surface extending from the upper surface and the lower surface, wherein the stretchable thin-film electrode is disposed on the self-healing elastomeric polymer substrate and the self-healing elastomeric polymer substrate extends towards the wall surface and surrounds the wall surface and a portion of the upper surface to form an embedded-anchored electrode device, and wherein the bioadhesive hydrogel layer is formed by coating a bioadhesive hydrogel on the embedded-anchored electrode device.

2. The shape-deformable and elastic bioadhesive electronic device of claim 1, wherein the self-healing elastomeric polymer material is a thermoplastic material.

3. The shape-deformable and elastic bioadhesive electronic device of claim 1, wherein the self-healing elastomeric polymer material is a material that is elastic and capable of self-healing.

4. The shape-deformable and elastic bioadhesive electronic device of claim 1, wherein the stretchable thin-film electrode device comprises a conductive pattern disposed on a surface of a substrate material, wherein the conductive pattern is formed by embossing or intaglio.

5. The shape-deformable and elastic bioadhesive electronic device of claim 1, wherein the bioadhesive hydrogel layer is one or more materials selected from the material groups that are able to be manufactured in a film form and are able to be hydrogelated in a moisture environment, among natural polymers containing aromatic substances and phenols.

6. The shape-deformable and elastic bioadhesive electronic device of claim 1, wherein a biological tissue to which the shape-deformable and elastic bioadhesive electronic device is applicable is one or more selected from the group consisting of brain tissue, spinal cord tissue, heart tissue, peripheral nerve tissue, vagus nerve tissue, and muscle tissue.

7. The shape-deformable and elastic bioadhesive electronic device of claim 1, wherein the thin-film electrode device is a thin-film multi-channel electrode device.

* * * * *